United States Patent [19]
Nelson

[11] Patent Number: 6,155,267
[45] Date of Patent: Dec. 5, 2000

[54] IMPLANTABLE MEDICAL DEVICE MONITORING METHOD AND SYSTEM REGARDING SAME

[75] Inventor: Teresa R. Nelson, Ham Lake, Minn.

[73] Assignee: Medtronic, Inc., Minneapolis, Minn.

[21] Appl. No.: 09/224,002

[22] Filed: Dec. 31, 1998

[51] Int. Cl.$^7$ ............................................. A61F 13/00
[52] U.S. Cl. ................................. 128/899; 600/509
[58] Field of Search ..................... 128/899, 897–898, 128/903; 600/300, 509, 510; 607/9, 28

[56] References Cited

U.S. PATENT DOCUMENTS

| | | | |
|---|---|---|---|
| 4,257,423 | 3/1981 | McDonald et al. | 128/419 PG |
| 4,360,030 | 11/1982 | Citron et al. | 128/702 |
| 4,556,063 | 12/1985 | Thompson et al. | 128/419 PT |
| 4,821,723 | 4/1989 | Baker, Jr. et al. | 128/419 D |
| 5,127,404 | 7/1992 | Wyborny et al. | 128/419 P |
| 5,131,388 | 7/1992 | Pless et al. | 128/419 D |
| 5,144,949 | 9/1992 | Olson | 128/419 PG |
| 5,158,078 | 10/1992 | Bennett et al. | 128/419 PG |
| 5,199,428 | 4/1993 | Obel et al. | 128/419 C |
| 5,207,218 | 5/1993 | Carpentier et al. | 128/419 PG |
| 5,246,014 | 9/1993 | Williams et al. | 607/122 |
| 5,312,453 | 5/1994 | Shelton et al. | 607/19 |
| 5,314,430 | 5/1994 | Bardy | 607/5 |
| 5,330,507 | 7/1994 | Schwartz | 607/14 |
| 5,331,966 | 7/1994 | Bennett et al. | 128/696 |
| 5,354,316 | 10/1994 | Keimel | 607/15 |
| 5,535,752 | 7/1996 | Halperin et al. | 128/670 |
| 5,536,752 | 7/1996 | Ducharme et al. | 514/602 |
| 5,545,186 | 8/1996 | Olson et al. | 607/14 |
| 5,564,434 | 10/1996 | Halperin et al. | 128/748 |

OTHER PUBLICATIONS

Introduction to Statistical Quality Control by Douglass C. Montgomery, John Wiley & Sons Print (1991) (pp. 114–118) sect. 4–3.5—4–4 & Earlier Editor of Book.

Artbauer, Application of Internal Statistical & Fuzzy Methods to the Evaluation of Measurments Metrologia 25, 81–86 (1988).

Chamberlin et al, Monitoring intensive care unit performance using statistical quality control charts, International Journal of Clinical Monitoring and Computing 10, 155–161 (1993).

Nelson et al., Application of Control Chart Statistics to Blood Pressure Measurement Variability in the Primary Care Setting Journal of the American Academy of Nurse Practitioners, 6(1). 17–28 (1991).

*Primary Examiner*—John P. Lacyk
*Attorney, Agent, or Firm*—Michael B. Atlass; Harold R. Patton

[57] ABSTRACT

An implantable medical device monitoring method and system monitors chronic data representative of at least one physiological parameter. The chronic data is monitored to detect changes in state of the at least one physiological parameter. Data associated with detected changes in state is stored within the implantable medical device. The detection of changes in state of the at least one physiological parameter is performed by establishing a baseline (e.g., a center reference line and upper and lower control limits), and then determining if the chronic data being monitored satisfies predetermined conditions (e.g., conditions based on the center reference line and the upper and lower control limits) indicative of a change in state of the at least one physiological parameter. The data stored in memory associated with the detected change in state of the at least one physiological parameter may, for example, include data representative of the center reference line and/or upper and lower control limits.

41 Claims, 10 Drawing Sheets

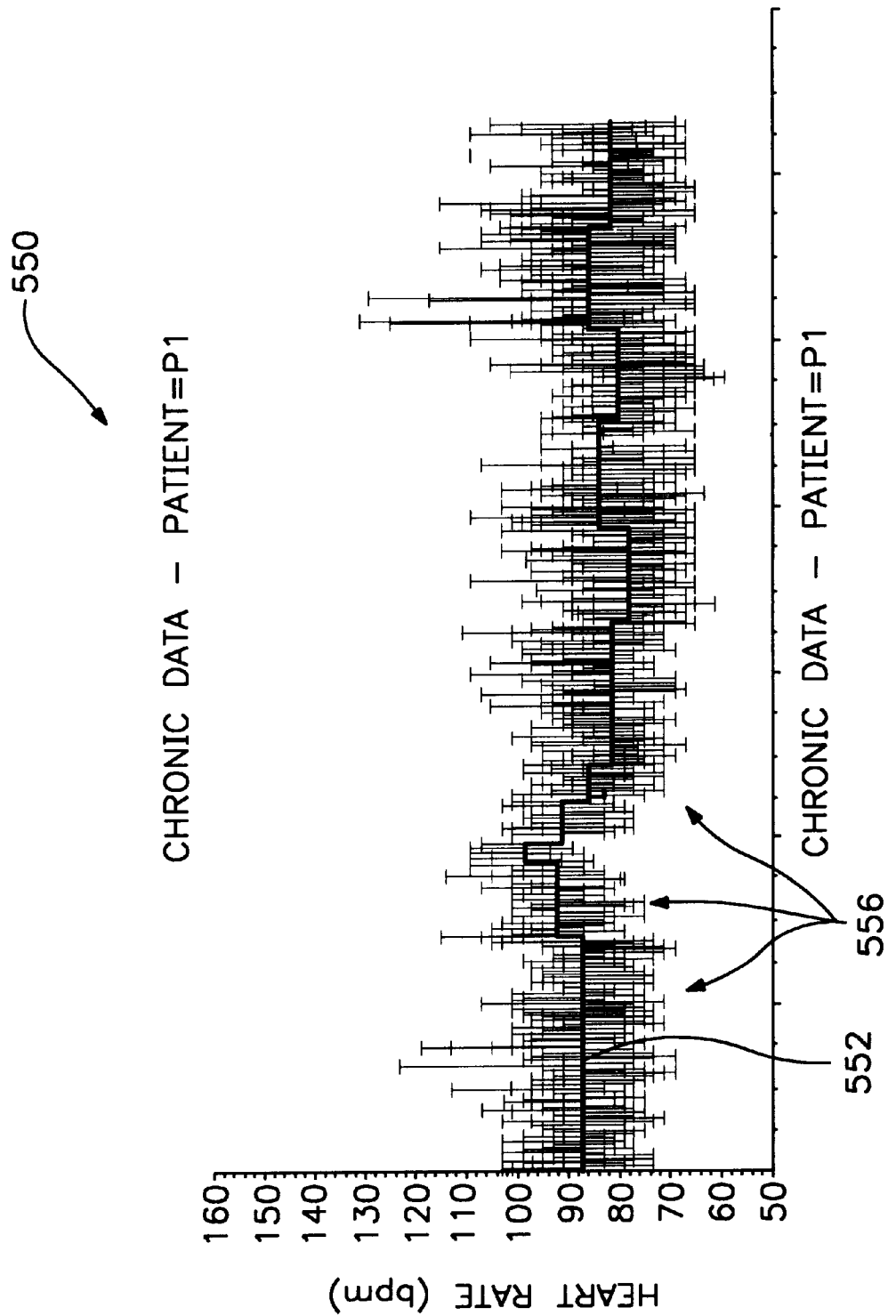

IMPLANTABLE MEDICAL DEVICE MONITORING METHOD AND SYSTEM REGARDING SAME

FIELD OF THE INVENTION

The present invention relates to implantable medical devices. More particularly, the present invention pertains to monitoring of physiological parameters by an implantable medical device with a reduction of the quantity of data to be stored thereby using statistical process control techniques.

BACKGROUND OF THE INVENTION

Various implantable medical devices are available for use in monitoring various physiological parameters. For example, U.S. Pat. No. 4,360,030 to Citron et al., entitled, "Apparatus For Monitoring And Storing A Variety Of Heart Activity Signals," issued Nov. 23, 1982, describes a heart monitoring and storing apparatus for evaluating heart activity signals. Further, for example, U.S. Pat. No. 5,535,752 to Halperin et al., entitled, "Implantable Capacitive Absolute Pressure And Temperature Monitor System," issued Jul. 16, 1996, describes a monitor that powers a sensor and which demodulates and stores absolute pressure and temperature data derived from signals generated by the sensor. Generally, an implantable device used for monitoring receives sensor output signals from one or more sensors, and monitors, records, and stores data representative of such signals when the device is implanted in a body and is operational. Further, generally, the implantable medical device used for monitoring includes transmitter/receiver circuitry for communicating information between the implanted device and a device external to the body, e.g., a programmer or external monitor.

For example, implantable monitoring devices, whether used solely as a monitoring device or in combination with other implantable therapeutic implantable devices, generally receive analog information from a sensor, store such information, and then transmit such information for usage external of the body. For example, the monitor may collect information regarding various physiological parameters of a patient such that a physician may scan records containing such information when the collected information is transmitted external to the body. The physician may then appropriately diagnose and treat the patient, e.g., assess changes in patient status, provide a therapy plan for the patient, recognize trends in such data, etc.

Generally, the most common method for storing and/or transmitting such sensor information is to first digitize the sensor information representative of one or more physiological parameters (i.e., change the analog signal to digital format) and then provide for storage of the digitized information in such a format. For example, as described in U.S. Pat. No. 5,535,752, a capacitive pressure sensing lead is employed with an implantable battery-powered monitor, including a microprocessor for implementing demodulation, data storage, and telemetry capabilities. The monitor samples and stores blood pressure data at programmed intervals and telemeters out the accumulated data to an external programmer on receipt of a command from an external device, such as in a manner which is conventional in implantable device technology. The monitor performs such periodic storage of digitized data related to physiological parameters, such as blood pressure and temperature, at a nominal sampling frequency which may be related to patient activity level. For example, such sampling frequency may be correlated to time and date and patient initiated event markers. As described in U.S. Pat. No. 5,535,752, blood pressure signals may be digitized and stored at a sample period of every 4 milliseconds or in other words, a 256 Hz sampling frequency. Further, for example, blood temperature signals may be digitized and stored once every sensed heart depolarization cycle. The digitized data values may be stored on a first-in first-out (FIFO) basis between periodic transmission of such data for permanent external storage outside of the device. External to the body, the data may then be analyzed to identify the portions of interest and to perform other diagnostic analysis of the accumulated data.

However, collecting and storing data for later communication to an external device, e.g., a programmer, at frequencies described above requires a large amount of memory to provide coverage for long periods of monitoring. For example, a typical storage period may be about 26 minutes for a single month of monitoring when the sampling frequency is approximately beat by beat, i.e., a sample taken every cardiac cycle. This becomes an undesirably large data set over the life of the implanted device.

Further, within such a data set there is a large variation in the data representative of the physiological parameter making it difficult to recognize a change or trend in any given physiological parameter. In other words, it is difficult to quantify and objectify the change within such large amounts of data.

In addition, such a large amount of data to be stored requires an undesirably large memory capacity, e.g., a large memory device, a large number of integrated circuits, etc. Such a large amount of memory is particularly undesirable for a small-sized implantable medical device and may cause excessive current drain from the battery during operation. Further, the large quantity of data collected and stored may require an undesirable amount of time to uplink such data to an external device. Although compression techniques are available, such compression techniques generally require extensive processing power which is typically not suitable for use in implantable medical devices.

SUMMARY OF THE INVENTION

The present invention provides for data reduction in a monitoring system. Further, such monitoring provides a solution to the problem created by the collection of a large amount of data over the implanted life of the device; where such large amounts of data include significant variation. Such variation makes it difficult to identify when a given physiological parameter has changed or is part of an expected variation. The present invention solves this problem by providing a manner of objectifying change, such that changes in the chronic data provided can be identified along with providing a reduction in the amount of data.

An implantable medical device monitoring method according to the present invention includes providing at least one sensor output signal to an implantable medical device and providing chronic data representative of at least one physiological parameter based on the at least one sensor output signal. A baseline is established representative of an initial state of the at least one physiological parameter using chronic data provided in an initial sample time period. The chronic data is monitored to detect a change in state of the at least one physiological parameter relative to the baseline and data associated with a detected change in state of the at least one physiological parameter is stored within the implantable medical device. The baseline is reestablished for the at least one physiological parameter if a change in state is detected using chronic data available upon or after detection of the change of state. The monitoring of the chronic data to detect changes in state, the storing of data associated with detected changes in state, and the reestablishing of the baseline if changes in state are detected are repeated.

In one embodiment of the method, the monitoring of the chronic data includes providing predetermined conditions indicative of a change in state of the at least one physiological parameter relative to the baseline. A change in state of the at least one physiological parameter relative to the baseline is detected if the predetermined conditions are satisfied.

In another embodiment of the method, the establishment of the baseline for the at least one physiological parameter includes determining a center reference line level using an average of a plurality of sample points representative of the chronic data in the initial sample time period. Further, an upper control limit and a lower control limit relative to the center reference line level is determined based on an average of standard deviations generated for the plurality of sample points.

In yet another embodiment of the method, storing data associated with the detected change in state of the at least one physiological parameter may include storing the center reference line level upon detection of a change in state of the at least one physiological parameter. Further, such storing of data may include storing the upper and lower control limits upon detection of a change in state of the at least one physiological parameter.

In other embodiments of the method, the method may include controlling a therapeutic device in response to the detection of one or more changes in state of the at least one physiological parameter and may include controlling an alarm in response to the detection of one or more changes in state of the at least one physiological parameter.

Another implantable medical device monitoring method according to the present invention includes providing chronic data to an implantable medical device representative of at least one physiological parameter, monitoring the chronic data to detect changes in state of the at least one physiological parameter, storing data associated with detected changes in state within the implantable medical device, and discarding the chronic data monitored to detect changes in state of the at least one physiological parameter.

An implantable monitoring system for monitoring at least one physiological parameter according to the present invention is also described. The system includes at least one sensor to provide an output signal representative of the at least one physiological parameter and an implantable monitoring device having memory to store data. The implantable monitoring device receives the at least one sensor output signal and generates chronic data representative of the at least one physiological parameter. The implantable monitoring device includes processing circuitry for monitoring the chronic data to detect changes in state of the at least one physiological parameter and to store data associated with detected changes in state in the memory of the implantable monitoring device.

In one embodiment of the system, the processing circuitry further provides for establishing a baseline representative of an initial state of the at least one physiological parameter using a plurality of sample points representative of chronic data in an initial sample time interval, provides for detecting changes in state of the at least one physiological parameter relative to the baseline, and provides for reestablishing the baseline for the at least one physiological parameter if a change in state is detected. The baseline is reestablished using chronic data available upon or after detection of the change of state.

In another embodiment of the system, the detection of changes in state of the at least one physiological parameter relative to the baseline is effected using processing circuitry to compare sample points representative of the chronic data to the baseline (e.g., a center line and upper and lower control limits) and to determine if the comparison satisfies predetermined conditions (e.g., conditions based on the center reference line level, the upper control limit, and the lower control limit) indicative of a change in state of the at least one physiological parameter. Further, for example, the data stored in memory associated with the detected change in state of the at least one physiological parameter may include data representative of the center reference line level and/or upper and lower control limits.

BRIEF DESCRIPTION OF THE DRAWING

FIGS. 7A–7D are graphical illustrations for use in describing the monitoring method according to the present invention with respect to one particular physiological parameter being monitored by the implantable monitor system shown in FIG. 6.

DETAILED DESCRIPTION OF THE EMBODIMENTS

Figure 1:
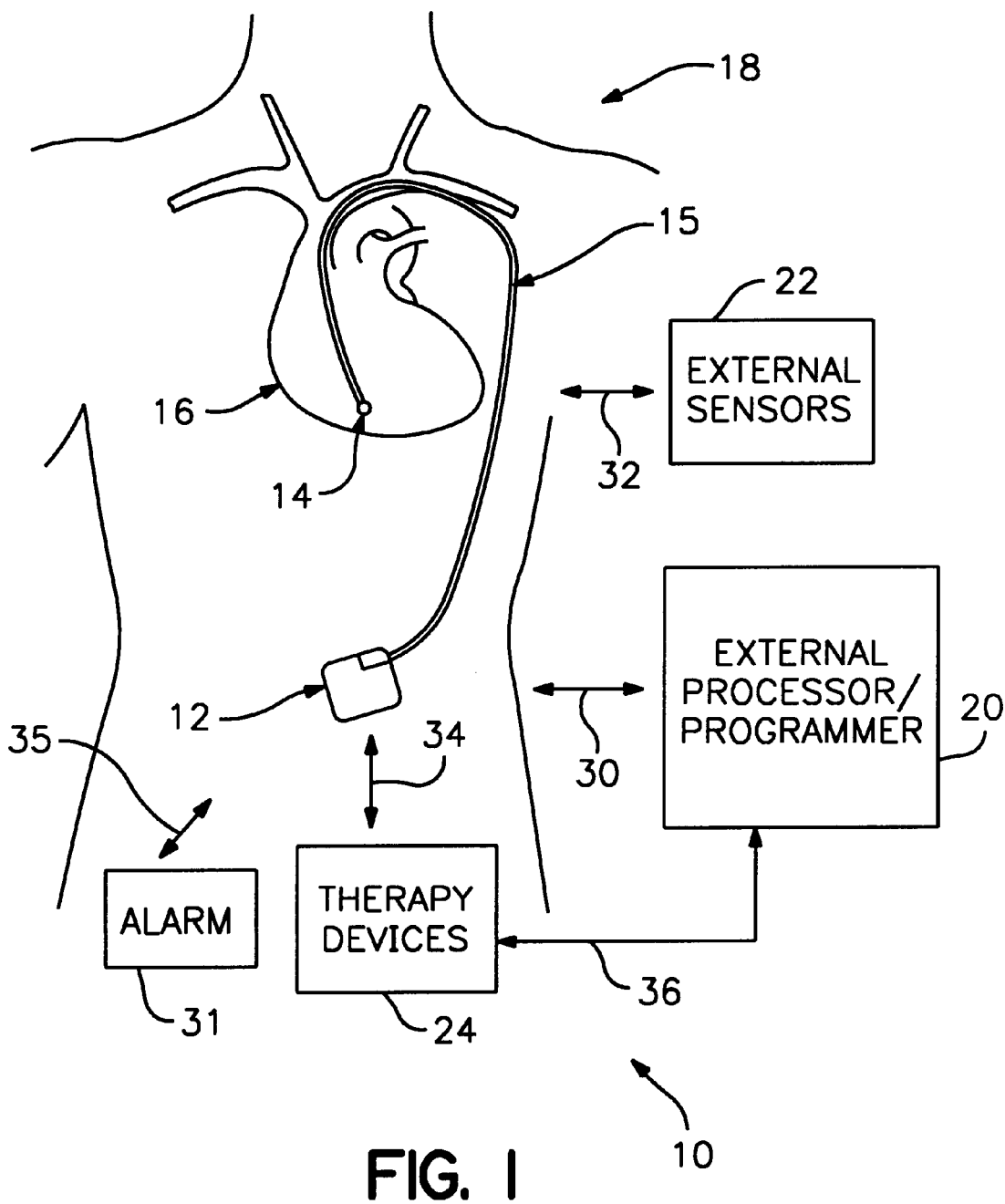
FIG. 1 is an illustrative diagram of an implantable medical device monitoring system according to the present invention where the device is implanted in a body.

FIG. 1 shows an implantable medical device monitoring system 10 which uses statistical process control, e.g., control chart concepts, to reduce chronic data representative of one or more physiological parameters collected by the monitor to clinically relevant information. By using such process control techniques to reduce the chronic data generated by the implantable medical device 12 of the system 10, a concise and easily implemented way to assess patient status from such chronic data is provided. The implantable medical device monitoring system 10 monitors chronic data to detect changes in a state of at least one physiological parameter. Instead of storing the chronic data, the implantable monitoring device 12 stores data associated with the detected changes in the state of the at least one physiological parameter. In other words, only the detected changes in state are recorded and the chronic data received by the monitoring device 12 is discarded. Such data associated with the detected changes in state of the at least one physiological parameter may then be communicated to an external device 20 of the system 10.

In addition to providing an objective manner of monitoring a change in state of the at least one physiological parameter, the reduction in the amount of data stored by the implantable monitoring device 12 is reduced, providing various advantages. For example, less data must be reviewed by a physician attending the patient to analyze specific trends in the data. Memory size may be reduced due to the reduced amount of stored data. More time efficient communication of such data between the implanted device 12 and an external device 20, e.g., a programmer, may be accomplished as less stored data must be communicated to the external device 20. Further, for example, the implantable device may be used over a longer period of time for monitoring purposes without the need to communicate such information to an external device 20 since a reduced amount of data over a period of time is stored in memory of the implanted device 12 compared to data stored in conventional monitoring devices.

It is possible in some circumstances that the chronic data not be discarded. For example, the chronic data may also be stored along with the detected changes in state of the physiological parameter and provided uplink to an external device 20. For example, some physicians may want to view the chronic data superimposed with the data associated with the changes in state such as shown illustratively in the graph of FIG. 7D. However, discarding of the chronic data provides the advantage of storing less data in the implanted monitoring device 12.

The implantable medical device monitoring system 10 generally includes implantable monitoring device 12 coupled to a sensor 14. Further, the system 10 includes external device 20, e.g., a programmer, for establishing a communication link 30 with implantable monitoring device 12 such that stored data therein can be communicated to the external device 20. Further, the implantable medical device monitoring system 10 may include external sensors 22 for communication with the implantable monitoring device 12 via communication link 32. In addition, the system 10 may include various therapy devices 24 for communication to either the implantable monitoring device 12 via communication link 34 or to external communication device 20 via communication link 36, and may further include one or more alarm devices 31 for communication with the implantable monitoring device 12 via communication link 35.

Generally, the implantable monitoring device 12 may be any monitoring device capable of implementing the monitoring method described herein. For example, implantable monitoring device 12 may be for monitoring heart rate activity, oxygen, right ventricle pressures, etc. Further, for example, the implantable monitoring device 12 may be implemented with an implantable cardiac pacemaker, such as that described in U.S. Pat. No. 5,158,078 to Bennett et al.; U.S. Pat. No. 5,312,453 to Shelton et al.; or U.S. Pat. No. 5,144,949 to Olson et al. In addition, further, the implantable monitoring device 12 may be implemented as a pacemaker-cardioverter-defibrillator (PCD) corresponding to any of the various commercially-available implantable PCDs. For example, the present invention may be practiced in conjunction with PCDs such as those described in U.S. Pat. No. 5,545,186 to Olson et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker et al. Alternatively, implantable monitoring device 12 may be implemented with an implantable neurostimulator or muscle stimulator such as that disclosed in U.S. Pat. No. 5,199,428 to Obel et al.; U.S. Pat. No. 5,207,218 to Carpentier et al.; or U.S. Pat. No. 5,330,507 to Schwartz, or may be implemented in an implantable monitoring device such as that disclosed in U.S. Pat. No. 5,331,966 to Bennett et al. or U.S. Pat. No. 5,535,752 to Halperin et al.

Further, for example, the implantable monitoring device 12 may be implemented in conjunction with a defibrillator, an implantable cardioverter-defibrillator (ICD), a brain stimulator, a gastric stimulator, a drug pump, an alarm device, another implantable monitoring device, or any other implantable device that may be used with a monitoring method such as described herein. Therefore, the present invention is believed to find wide application in any form of implantable medical device to monitor any physiological parameter which such a device may be collecting over time. Preferably, as will be described in further detail below, the implantable monitoring device 12 is an implantable hemodynamic monitor such as for implant in a patient with compromised hemodynamic function.

Figure 2:
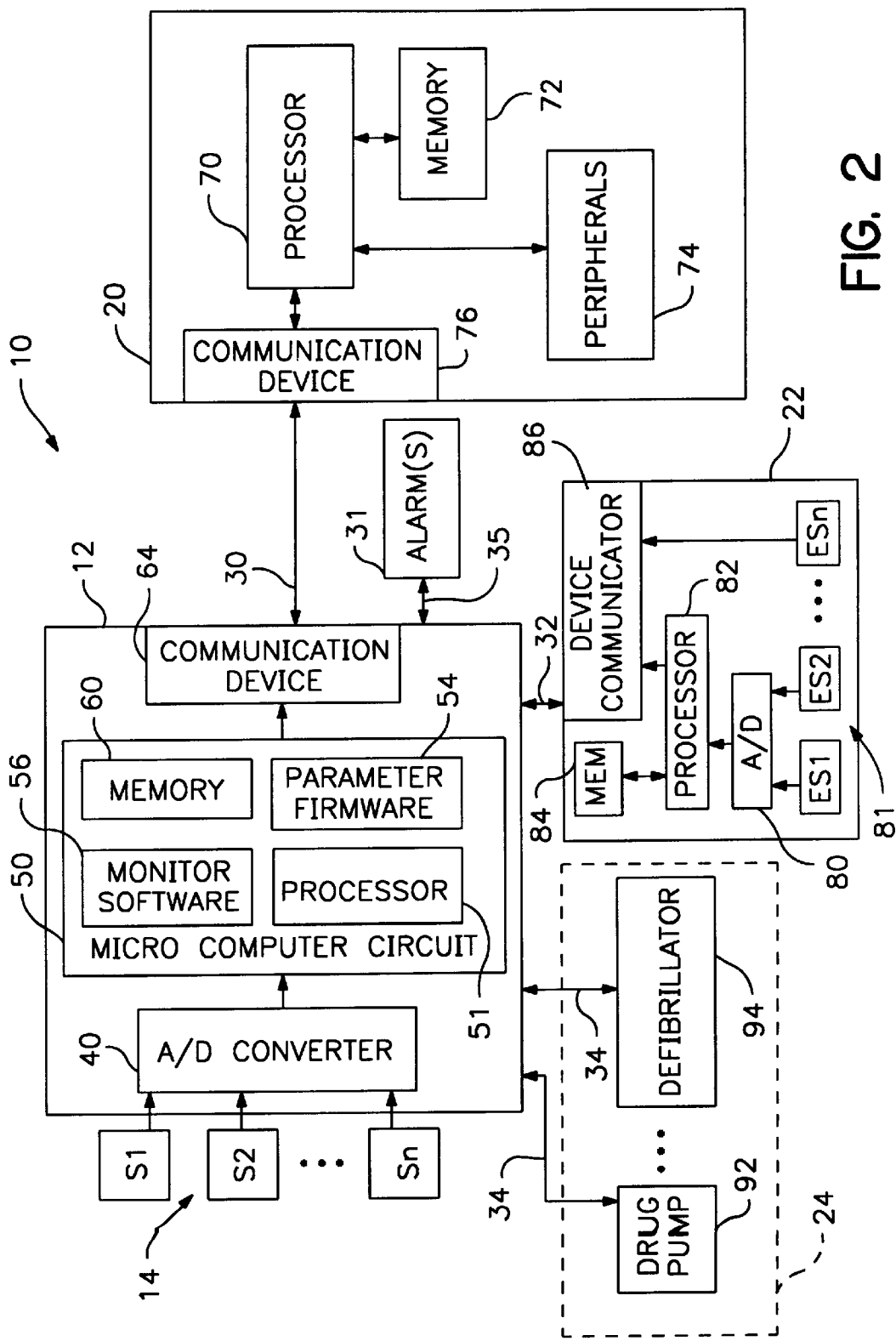
FIG. 2 is a block diagram of the implantable medical device monitoring system of FIG. 1 according to the present invention.

FIG. 2 is a simplified block diagram of the implantable medical device monitoring system 10 shown in FIG. 1 including implantable monitoring device 12 coupled to sensors 14, external communication device 20, external sensors 22, alarms 31, and therapy devices 24. As described above, implantable monitoring device 12 may be implemented in conjunction with various implantable medical devices. Generally, such an implantable monitoring device receives analog signals from one or more sensors 14, including sensors S1–Sn. Any sensor 14 may be used which provides an output signal representative of at least one physiological parameter. For example, as shown in FIG. 1, lead 15 extending externally from the housing of implantable monitoring device 12 is implanted transveneously into the right heart chamber in a manner like conventional pacing leads except that distal end of the lead 15 is a pressure sensor 14. However, such sensors 14 may be of any form capable of providing an output signal representative of a physiological parameter to be monitored. For example, various sensors are described in U.S. Pat. No. 5,564,434 to Halperin et al., entitled "Implantable Capacitive Absolute Pressure And Temperature Sensor," issued Oct. 15, 1996; and U.S. Pat. No. 5,246,014 to Williams et al., entitled, "Implantable lead system," issued Sep. 21, 1993.

Further, generally, the implantable monitoring device 12 includes an analog-to-digital (A/D) converter 40, a microcomputer circuit 50 including a processor 51 and memory 60, and a communication device 64. The A/D converter 40 converts the sensor output signal from one or more sensors 14 to digital information to be communicated to microcomputer circuit 50. Microcomputer circuit 50 includes physiological parameter firmware 54 and monitoring software 56. Generally, the microcomputer circuit 50 receives the converted digital data from the A/D converter 40 and applies algorithms of the physiological parameter firmware 54 to the digital data to calculate one or more physiological parameters which are of use for clinical analysis of the patient in which the implantable monitoring device 12 is implanted.

Physiological parameter firmware 54 may be used to calculate one or more physiological parameters from one or more sensor output signals. In other words, there can be more than one physiological parameter being calculated from a single sensor output signal and there may be some physiological parameters calculated from more than one sensor output signal. For example, in the case of a hemodynamic monitoring device, there may be eight or more physiological parameters calculated from a single output signal collected from a pressure sensor implanted in the right ventricle. Such physiological parameters may include right ventricle systolic pressure, right ventricle diastolic pressure, and right ventricle pulse pressure. Further, such parameters may include maximum positive dP/dt, maximum negative dP/dt, STI (time from r-wave to maximum negative dP/dt), PEI (time from r-wave to maximum positive dP/dt), and estimated pulmonary artery diastolic (ePAD) pressure. Three of these parameters, including right ventricle systolic pressure, right ventricle diastolic pressure, and estimated pulmonary artery diastolic pressure, are absolute pressure parameters and the information processed internally by the firmware must be merged with an external pressure reference which reads barometric data to generate usable physiological pressures.

The output signals from the one or more sensors 14 are preferably digitized and provided to microcomputer 50 at a predetermined sampling frequency. As such, physiological parameter firmware 54 provides chronic data representative of at least one physiological parameter based on the at least one sensor output signal. As used herein, chronic data refers to a continuous stream of data representative of at least one physiological parameter. The chronic data may be data provided at the same frequency as the sensor sampling frequency or may be provided at any other frequency. For example, pressure may be sensed by the sensor every beat of the cardiac cycle with the chronic data, e.g., systolic pressure, being based on an average of multiple sensed pressures and provided every hour or day. Such chronic data is continuously provided when the implantable monitoring device 12 is operational. As the implantable monitoring device 12 may be used for a variety of physiological parameters, the firmware 54 for calculating such parameters from the sampled sensor output signals will vary according to the one or more physiological parameters being monitored, e.g., heart rate, systolic pressure, etc.

Rather than storing the chronic data representative of one or more physiological parameters to memory 60 for periodic communication therefrom via communication device 64 to an external device 20, the chronic data is provided for operation thereon by monitoring software 56. Generally, and as will be described further below, monitoring software 56 may monitor one or more physiological parameters for which sample points are provided by firmware 54. However, for simplicity in the description provided herein, the monitoring software 56 shall be limited to the monitoring of a single physiological parameter.

Figure 3:
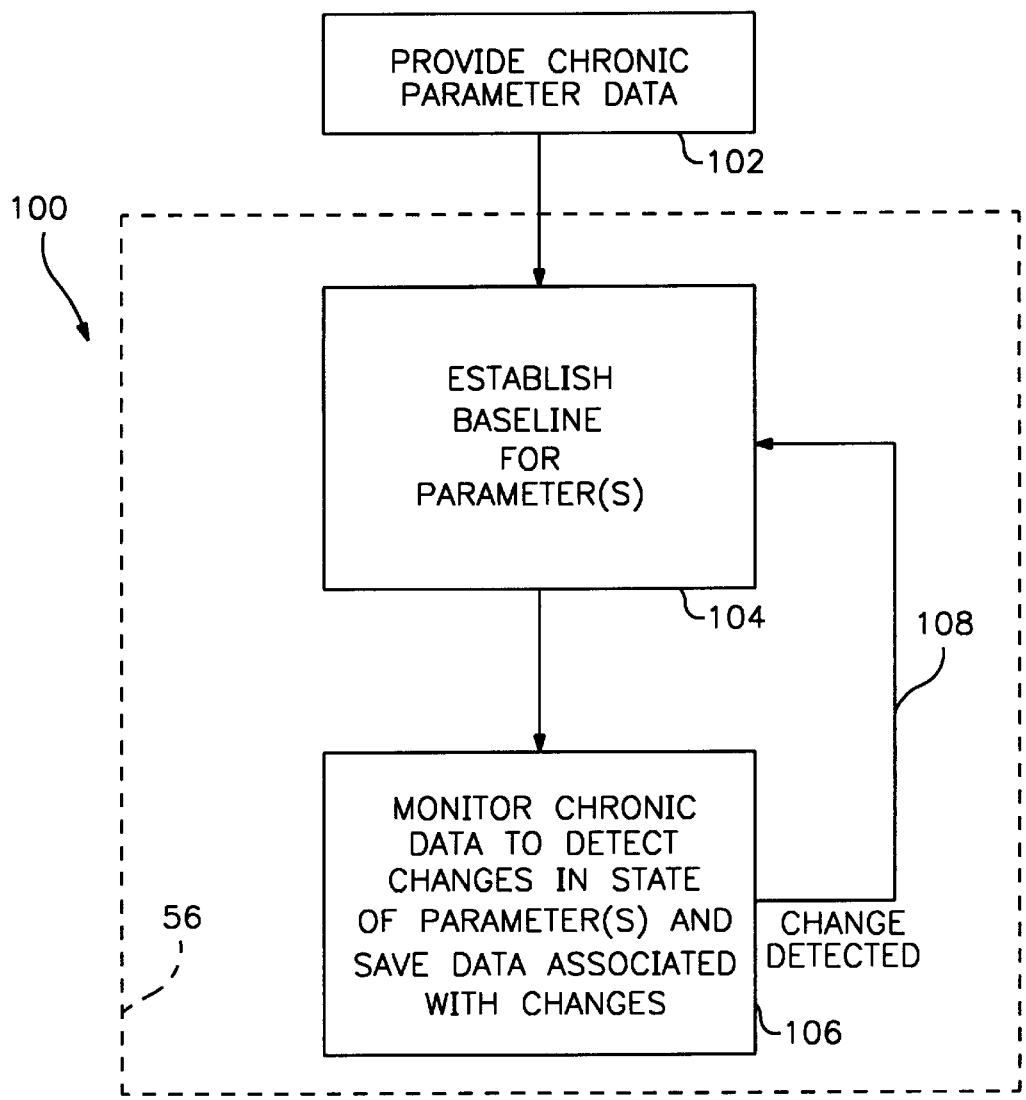
FIG. 3 is a general flow diagram of a monitoring method implemented by the system shown in FIGS. 1 and 2 according to the present invention.

As shown by the general flow diagram of FIG. 3, the monitoring method 100 according to the present invention includes providing the chronic data representative of the physiological parameter being monitored (block 102) to monitoring software 56. Monitoring software 56, using an initial sample of chronic data provided by firmware 54, establishes a baseline for the physiological parameter being monitored (block 104). By establishing a baseline for the physiological parameter being monitored (block 104), the chronic data and its variability is reduced to an underlying trend level, i.e., a particular physiological level or state. For example, as later described herein, the baseline may be established by taking daily averages of the chronic data to generate daily average sample points and then averaging the daily average sample points over a particular period of time. The established baseline, e.g., a trend level for the particular physiological parameter, is saved in memory 60 along with an indication of date and time.

Using the established baseline, e.g., the calculated underlying trend level for the physiological parameter, monitoring software 56 monitors the chronic physiological parameter data relative to the established baseline to detect changes in state of the physiological parameter (block 106). In other words, the physiological parameter is monitored for an indication that the trend level of the physiological parameter, i.e., the established baseline, is discontinuing and a new trend is beginning, i.e., a change in state of the physiological parameter is occurring with a new baseline.

As used herein, a change in state of the physiological parameter refers to the satisfaction of one or more various conditions set relative to the established baseline which indicates that the physiological parameter of the patient has attained a level which according to statistical process control is outside control limits for the established baseline. Such conditions are used to judge whether the chronic data representative of the physiological parameter is indicative of a change in state of the physiological parameter.

If a change of state in the physiological parameter is detected, a new baseline is re-established, as shown by flow line 108, using a sample of the chronic data available upon and/or after detection of the change in state. This new re-established baseline is then stored in memory 60 and the chronic data is further monitored (block 106) to detect further changes in state relative to the re-established baseline. The detection of changes in state, re-establishment of the baseline, and storage of data associated with the re-established baselines continues in real-time in the implantable monitoring device 12.

As described above, the same monitoring software 56 may be applied to any and all of the physiological parameters calculated by the firmware 54 based on output signals from the one or more sensors 14. By using this monitoring method 100, an objective means of identifying changes in the chronic data is provided and the chronic data is reduced in size, e.g., to calculated baseline data, for convenient and effective storage in memory 60. Preferably, the chronic data, as provided in block 102, is discarded. The established baseline and re-established baselines saved upon detection of changes in state of the physiological parameter being monitored provide the data to be communicated to an external device 20, e.g., a programmer, processor, etc.

Data transmission to the external device 20 from the implanted device 12 may be accomplished using any type of communication link 30 capable of communicating data between the implantable device 12 having a communication device 64 and an external device 20 which includes a communication device 76 and which is external to the body in which the implantable medical monitoring device 12 is implanted. For example, the communication link 30 may be established by way of a communication device 64 including a telemetry antenna and associated transmitter/receiver circuitry which serves to receive and demodulate downlink telemetry from communication device 76 of external device 20 and to also transmit uplink telemetry from communication device 64 to communication device 76 of the external device 20. For example, the communication device 64 may include circuitry for demodulating and decoding downlink telemetry such as that disclosed in U.S. Pat. No. 4,556,063 issued to Thompson et al. and U.S. Pat. No. 4,257,423 issued to McDonald et al. In addition, the communication device 76 of external device 20 may be provided according to U.S. Pat. No. 5,127,404 issued to Wyborny et al. Such communication links 30 may be capable of transmitting stored data representative of the changes in state of the physiological parameters as well as real-time sensed signals. One skilled in the art will recognize that any communication link 30 may be used, including acoustic communication links, inductive coupling, and capacitive coupling, in addition to RF telemetry.

Generally, the external device 20 shown illustratively in FIGS. 1 and 2 is an apparatus having at least a communication device 76. For example, the communication device 76 may include transmitter/receiver circuitry and an antenna for transmitting and receiving uplink telemetry from the implanted device 12. Further, for example, the external device 20 may be a programmer including a conventional telemetry system used for receiving information from an implantable medical device and transmitting information thereto. Generally, such programmers are used to adjust parameters of implantable devices and typically include a processor 70 and associated memory 72 for overall control of the external device 20. In addition, such programmers typically have various peripherals 74, such as graphic displays, keyboards, or other user interfaces for data entry and device control by operator manipulation. Further, such programmers may include printers or plotters to allow the user to control, evaluate, and document the extensive capabilities of the monitoring device 12 from which it is receiving information. For example, such printers and plotters may provide simplified trend or change in state charts as will be described further herein with reference to FIGS. 7A–7D. Such programmers may include Medtronic physician/patient programmers such as, for example, Medtronic Model No. 9760 programmer or Medtronic Model No. 9790 programmer.

Implantable medical device monitoring system 10 as shown in FIG. 2 may further include external sensors 22 and additional implantable or external medical devices 24 which may be controlled as a function of the information provided by monitoring device 12. External sensors 22 may include one or more sensors 81. The one or more sensors 81 may communicate directly with device communicator 86 or may be provided to A/D converter 80 for digitization with the resulting digital data being provided via processor 82 and associated memory 84 to device communicator 82. For example, one of the sensors 81 may be an external sensor for providing an external atmospheric pressure reference. Such barometric data may be necessary to calculate desirable parameters in conjunction with the absolute pressure parameters in the case of a hemodynamic monitoring device. The external sensor information may be communicated to the implanted device 12 using RF telemetry or any other communication link 32 for communicating between an external sensor and the implantable monitoring device 12 such as those described previously herein.

The therapeutic implantable or external medical devices 24 may include any controllable therapeutic device. For example, such devices may include pacemakers, a brain stimulator, a defibrillator, a neurostimulator, a pacemaker/cardioverter/defibrillator, a cardioverter/defibrillator, a muscle stimulator, a gastric stimulator, another monitoring device, an alarm, or a drug pump. According to the present invention, such devices 24 may be controllable as a function of the change of state information stored in memory 60 and/or available from monitoring software 56. For example, such change of state information may be used as a triggering point for sending a control signal to a drug pump 92 for changing a dosage level. Likewise, such change of state information may be used in determining whether therapy by a defibrillator 94 is required. Further, another additional monitoring device or the monitoring device carrying out the monitoring method according to the present invention may be controlled based on the change in state information. For example, the sample periods for determining a baseline as further described below may be adjusted, the sampling frequency for monitoring may be increased, etc.

The communication link 34 between the implantable or external devices 24 and the implantable monitoring device 12 may be provided in any number of ways. For example, such information may be transmitted between the two devices via RF links, by acoustic links, etc. The change of state information stored in memory 60 may also be communicated via communication device 64 to the external device 20 such that a physician can react to such change of state information and deliver appropriate therapy via programming of the external or implantable devices 24. Such communication from the external device 20 to the external or implantable device 24 may be provided via communication link 36 (shown in FIG. 1).

The one or more alarms 31 may be activated based on change in state information, such as warning information or out of control information as further described below. The alarm may be an audible alarm, a tactile alarm, or any other alarm for notifying the patient being monitored or another person that some sort of action is desirable due to detected changes in state. For example, one or more different alarm states may be use to give notice that a physician should be contacted, a particular therapy is needed, or uplink of data should be performed.

Figure 4:
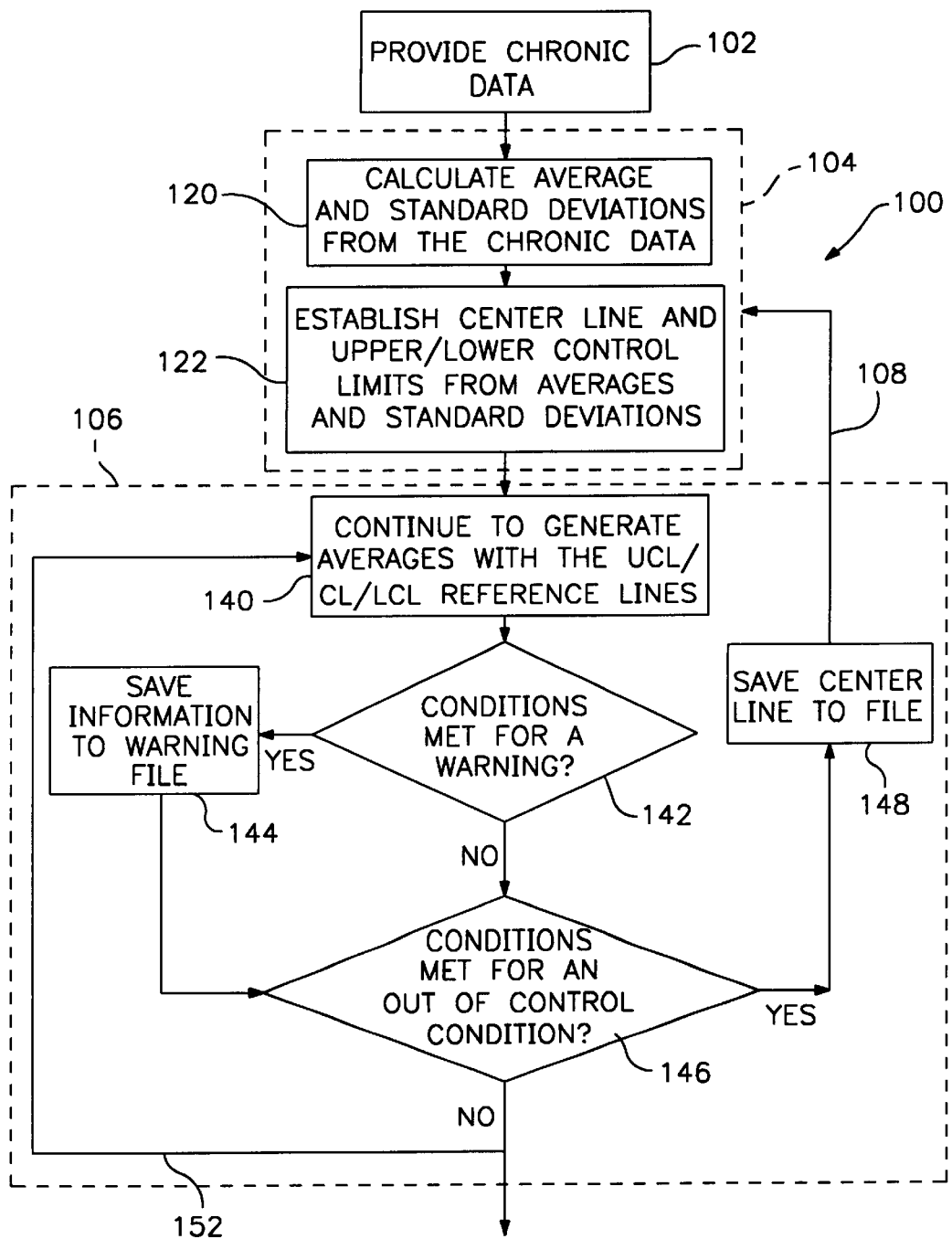
FIG. 4 is a more detailed flow diagram of an embodiment of the monitoring method of FIG. 3.

FIG. 4 is a more detailed flow diagram of one embodiment of the monitoring method 100 shown in FIG. 3. Generally, the monitoring method 100 of FIG. 4 uses a control chart approach for monitoring chronic data provided to the implantable monitoring device 12 consistent with statistical process control techniques. As such, the monitoring method 100 shown in FIG. 4 shall be described with reference to the generalized control chart 200 of FIG. 5. The chronic data representative of the physiological parameters is provided (block 102) for operation thereon by the monitoring software. For example, an oxygen sensor may have an oxygen sampling interval such as 2, 4, 6 . . . 30 seconds, with the chronic data including values for physiological parameters based on one or more oxygen levels sampled at such frequencies, e.g., an average, mean or median of one or more sampled levels. Further, for example, a pressure sensor may be sampled with a pressure sampling interval such as every heart beat, 2, 4, 6 . . . 30 seconds, with the chronic data including values for a physiological parameter, e.g., right ventricular systolic pressure, based on one or more pressure levels sampled at such frequencies.

Figure 5:
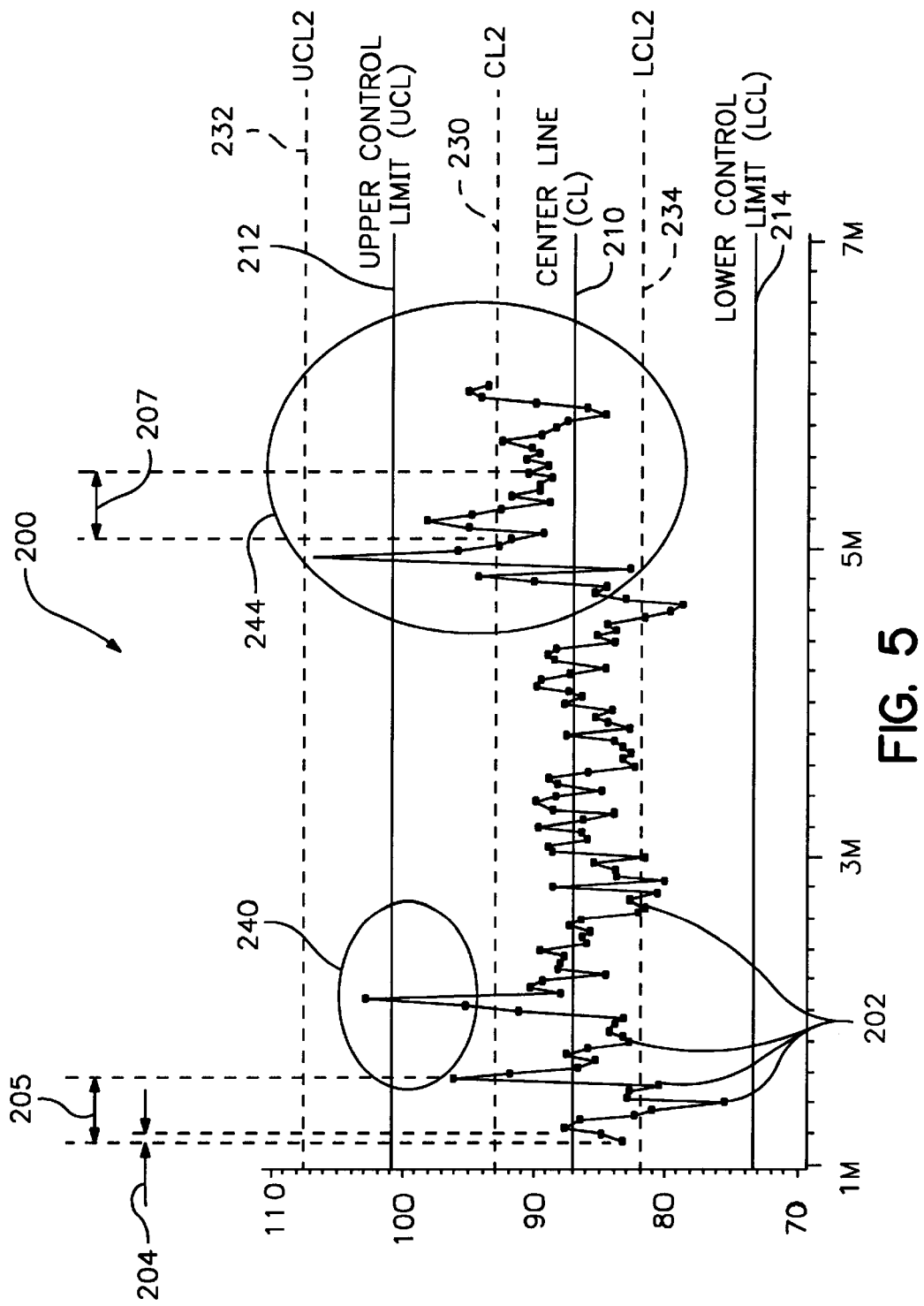
FIG. 5 is an illustrative graphical illustration for use in describing the monitoring method shown in FIGS. 3 and 4 according to the present invention.

To begin the reduction of such chronic data, the baseline for the physiological parameter is established (block 104). To establish the baseline for the physiological parameter being monitored (block 104), averages and standard deviations are calculated from the chronic data (block 120). Thereafter, a baseline, including for example, a centerline and one or more control limits are established based on such averages and standard deviations (block 122). The chronic data, e.g., physiological parameter levels provided at a sampling frequency, is averaged (e.g., the mean of such levels is generated) over sample point time intervals 204 (FIG. 5) to generate average sample points 202 representative of the physiological parameter level over such a time interval. For example, the chronic data may be averaged over a periodic time interval (e.g., hourly, daily, weekly, monthly, etc.), or may be averaged over a non-periodic interval (e.g., a programmable interval such as a pseudorandom time interval, a night interval and a daytime interval, etc.) resulting in each average sample point 202. Preferably, the average is taken over a periodic time interval. In other words, each average sample point 202 is a summary of the chronic data over a particular sample point time interval 204. In FIG. 5, the sample point time interval is a daily interval so each sample point 202 is an average daily sample point representative of a physiological parameter for a one day period.

One skilled in the art will recognize from the description provided herein that the sampling frequency of one or more of the sensors may be at a low level such that each sampled point 202 may actually coincide with the sampling of the sensor. As such, no averaging would be necessary to get a sample point 202. Likewise, in the other direction, the sampling frequency may be very high and the sample point 202 may be an average of a substantial number of sampled signals from one or more of the sensors.

In addition to the average sample points 202, standard deviations of the chronic data are calculated. Such standard deviations are calculated for the chronic data within the sample time intervals 204 relative to the average sample point determined for the particular sample point time interval. For example, if a daily average sample point is determined then a standard deviation (referred to herein as "sigma") for the chronic data used to generate the daily average sample point is provided to represent the variability of such daily chronic data relative to the daily average sample point.

From the average sample points and standard deviations computed relative thereto, a centerline 210 and one or more control limits, e.g., upper control limit (UCL) 212 and lower control limit (LCL) 214, as shown in FIG. 5, are established. The centerline (CL) 210 is established as an average of a collection of average sample points 202 over an initial centerline sample time period 205. Preferably, such a centerline sample time period 205 will generally be a multiple of the sample point time interval 204. For example, if the sample point time interval 204 is for generating a daily average sample point, the centerline sample time period 205 would be for averaging a collection of daily average sample points, e.g., fifteen daily average sample points. Generally, the initial centerline represents the current state of the physiological parameter being monitored. As described further below, upon detection of a change in state of the physiological parameter being monitored, the centerline is re-established to represent the then-current state of the physiological parameter.

Preferably, the one or more control limits generated relative to the centerline (CL) 210, include at least one upper control limit (UCL) 212 and at least one lower control limit (LCL) 214. The control limits are established so that predetermined conditions can be set using such control limits for determining if a change in state of the physiological parameter being monitored has occurred. However, such control limits may take one of various forms including the use of multiple upper and multiple lower limits. For example, there may be two upper control limits and two lower control limits. Such limits may be programmable over time. For example, the limits may be set higher for when a patient is asleep as opposed to when the patient is awake. As such, the present invention is not limited to any particular type of control limit (e.g., straight line control limit versus a parabolic or a multiple level control limit), is not limited to any particular number of control limits (e.g., two upper or three upper control limits), and is not limited to any set or fixed control limit (e.g., fixed value versus programmable values changing over time).

There may be various manners of choosing the upper and lower control limits. Such choice is a trade-off between Type-1 and Type-2 error. With narrower control limits relative to the centerline (CL) 210, the chance of Type-1 error increases, i.e., a sample point falling beyond the control limits without a change in state of the patient of the physiological parameter actually occurring. Widening the control limits increases Type-2 error, i.e., continuing to believe that the patient is functioning at a current state when actually the patient's physiological parameter has changed to a new state but due to the widened control limits a change in state is not indicated or detected.

Preferably, as shown in FIG. 5, the control limits include the upper control limit (UCL) 212 and the lower control limit (LCL) 214 computed relative to the centerline 210 based on the standard deviations previously computed for average sample points in the centerline sample time period 205. For example, if sample points 202 are daily averages and the collection of daily averages to be averaged for computing centerline 210 is five days, then the average standard deviation (referred to herein as sigma) of the collection of daily standard deviations over the five day period may be multiplied by a factor to compute the upper and lower control limits 212, 214. For example, the control limits may preferably be calculated as (±) 3-sigma control limits, i.e., three times sigma, or in other words, three times the average standard deviation within the centerline sample time period 205. There may also be a multiplier designed to reduce bias in the estimate of the standard deviation. This multiplier would be based in statistical theory and is usually related to the sample size (n) for which the deviation is estimated.

Generally, establishing control limits revolves around the normality assumption. For example, if it is assumed that the mean of the physiological parameter is normally distributed, 99.73% of the average sample points should fall between the upper control limit (UCL) 212 and the lower control limit (LCL) 214 when such limits are established as 3-sigma control limits. Under these conditions, the probability of Type-1 error is 0.0027, meaning 27 out of 10,000 sample points 202 will fall outside the limits and possibly signal a change in state of the physiological parameter being monitored when the state of the physiological parameter has not actually changed. Although the use of ±3-sigma limits for the upper control limit (UCL) 212 and the lower control limit (LCL) 214 is preferred, various other limits, e.g., 2-sigma limits, 1-sigma limits, etc. may be used as well. The type of physiological parameter being monitored may determine the manner in which the upper control limit (UCL) 212 and the lower control limit (LCL) 214 are calculated.

One skilled in the art will recognize that for estimating the standard deviations, various techniques exist. For example, either the range of the sample points or the actual sampled standard deviation may be used as would be known to one skilled in the art. Multipliers may be used to reduce bias in the estimate.

With the centerline (CL) 210 and upper/lower control limits (UCL/LCL) 212, 214 being calculated from the averages and standard deviations within the centerline sample time period 205 (block 122), average sample points 202 are continually generated for the physiological parameter being monitored (block 140). Such generated average sample points 202 are compared, e.g., plotted, to the centerline 210 and upper/lower control limits 212, 214 to determine if a change in state of the physiological parameter is occurring (block 142, 146).

Various predetermined conditions are set to determine whether such change in state of the physiological parameter is occurring. In other words, various conditions indicative of a change in state of the physiological parameter being monitored are provided. Such predetermined conditions are consistent with conditions set forth in statistical quality control techniques for determining out of control processes. For example, various conditions set forth in the book entitled, *Introduction to Statistical Quality Control*, by Douglas C. Montgomery, John Wiley & Sons Print, (1991), may be used to determine whether a change in state of the physiological parameter from the centerline level 210 has occurred or is likely to occur.

Such predetermined conditions may include conditions for determining whether a warning should be noted and predetermined conditions for detecting whether a change in state of the physiological parameter has occurred. With predetermined warning conditions set, it can be determined whether such warning conditions are met by the average sample points 202 representative of the chronic data (block 142). For example, warning conditions may be provided indicating that something worth paying attention to may be occurring. As an illustration, a specific condition for issuing a warning (block 142) may be that an average sample point 202 is above the upper control limit 212 or below the lower control limit 214. If such a condition is met by the sample point calculated from the chronic data, then information associated with the warning condition is saved to a warning file (block 144) to be later communicated to an external device 20. For example, data associated with such a warning may be a data mark in the file including the date and time that such a warning event occurred. As shown in FIG. 5, a warning event 240 is noted when a sample point was above the upper control limit 212. Further, ±2-sigma limits or ±1-sigma limits may be established as warning limits such that if such limits are exceeded, a warning is noted. After the average sample points 202 are monitored to detect whether warning events have occurred, then the sample points 202 are monitored to detect whether a change in state of the physiological parameter being monitored has occurred.

To detect whether a change in state of the physiological parameter is or has occurred, the sample points 202 generated from the chronic data are monitored to determine whether predetermined out of control conditions have been satisfied indicating a change in state of the physiological parameter being monitored (block 146). Such out of control conditions indicative of a change in state of a physiological parameter, and the above warning conditions, are grounded in the rules of probability. Such predetermined out of control conditions may take various forms. For example, the basic criterion for an out of control condition is that one or more points are outside of the upper and lower 3-sigma control limits 212, 214. However, other supplemental out of control conditions may include, but are not limited to, rules that are widely used in the practice such as: one or more points above the upper 3-sigma control limit 212; one or more points below the lower 3-sigma control limit 214; a run of at least eight consecutive sample points above the centerline 210; a run of at least eight consecutive sample points below the centerline 210; two of three consecutive points above an upper 2-sigma warning limit but still below the upper 3-sigma control limit 212; two or three consecutive sample points below a lower 2-sigma warning limit but still above the lower 3-sigma control limit 214; four of five consecutive points above an upper 1-sigma warning limit; four of five consecutive sample points below a lower 1-sigma warning limit; an unusual or nonrandom pattern in the sample points; and one or more points near warning limits or the 3-sigma control limits.

The different possible conditions indicative of a change in state of the physiological parameter are numerous and the present invention is not intended to be limited to those listed herein. However, preferably, the out of control conditions include a run of at least fifteen consecutive sample points above the centerline 210, a run of at least fifteen consecutive sample points below the centerline 210, a run of eight consecutive sample points above the centerline 210 with at least one of the sample points being above the upper control limit 212, and a run of eight consecutive sample points below the centerline 210 with at least one of the sample points being below the lower control limit 214.

As described above, one skilled in the art will recognize from the description herein that more than one upper control limit and lower control limit may be used according to the present invention. For example, such limits may include ±1-sigma limits, ±2-sigma limits, and ±3-sigma limits. With use of such multiple control limits, the possibilities for the predetermined conditions set to indicate a change in state of the physiological parameter being monitored further increase. For example, in the case of using ±2-sigma limits and ±3-sigma limits, the conditions indicative of a change in state may be a run of 3 consecutive sample points 202 outside the 2-sigma control limits with one sample point beyond the 3-sigma control limit.

If the conditions are satisfied for an out of control condition (block 146), then data representative of the centerline 210 is saved to memory 60 and the monitoring method proceeds in re-establishing the baseline as generally shown by flow line 108. Further, data representative of one or more of the control limits may also be stored as an indicator of average variability. For example, the upper and lower control limits may be stored. As such, one skilled in the art will recognize from the description provided herein that various types of data associated with a detected change in state may be saved.

The re-establishment of the baseline is performed by recalculating averages and standard deviations for chronic data within a centerline sample time period such as time period 207 as shown in FIG. 5, e.g., a time period which may be equivalent in length to centerline sample time period 205, using chronic data available upon or after it has been determined that such out of control conditions are met, i.e., that a change in state of the physiological parameter has been detected.

Circle 244 in FIG. 5 shows an out of control condition being satisfied indicative of a change in state of the physiological parameter being monitored from the state represented by centerline (CL) 210. Both predetermined conditions of more than fifteen consecutive sample points 202 above the centerline 210 and a run of eight consecutive sample points 202 above centerline 210 with one of such sample points 202 of the run of eight points being above the upper control limit 212 are satisfied.

As shown in FIG. 5, the re-established centerline upon detection of an out of control condition indicative of a change of state of the physiological parameter is shown as centerline (CL2) 230. Computing an upper control limit and lower control limit relative to the re-established centerline 230 results in upper control limit (UCL2) 232 and lower control limit (LCL2) 234. Such centerlines and control limits are re-established in substantially the same manner as described above with regard to the initial centerline and control limits.

If the conditions for the out of control condition are not satisfied, then the chronic data is continued to be monitored as represented by line 152. The chronic data is continually monitored to look for warnings (block 142) and/or out of control conditions (block 146).

Generally, by using the method described herein, the chronic data is reduced to a collection of centerlines, and possibly upper and lower control limits, as changes in state of the physiological parameter are detected. The stored data representative of each centerline established and/or re-established describes a period in which an out of control condition was not detected, i.e., a particular period of time the physiological parameter was in a particular state.

For a physician, once this centerline data, and possibly warning and upper and lower control limit data, is communicated to an external device 20, the centerlines may be displayed in various forms. For example, a tabular display or a graphical display may be used. In a graphical display, centerlines over a period of time may be illustrated, as will be described further below with reference to FIGS. 7A–7D.

In addition to monitoring average sample points, it may also be beneficial to monitor the standard deviations. For example, monitoring the standard deviations may indicate whether the variability of the chronic data has changed. Data indicative of such changes may also be stored and provided to the physician via communication to an external device 20.

Figure 6:
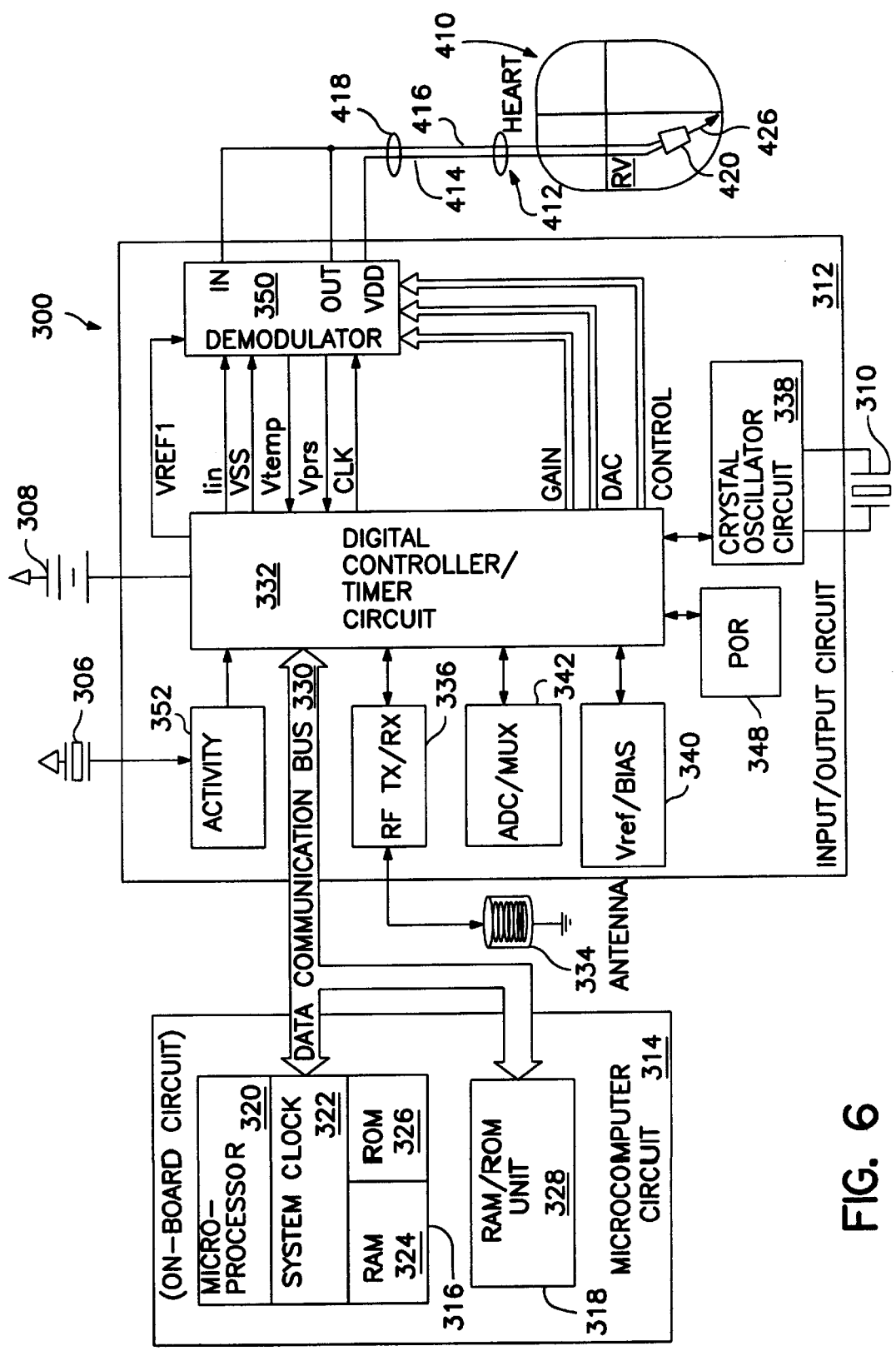
FIG. 6 is a block diagram of one embodiment of an implantable blood pressure monitor and lead system which may employ the monitoring method according to the present invention.

FIG. 6 is a block diagram of one embodiment of an illustrative implantable blood pressure monitor and lead system which may employ the monitoring method 100 according to the present invention. The simplified block diagram shows the patient's heart 410 in relation to a pressure sensing lead 412 and monitor 300. The lead 412 has first and second lead conductors 414 and 416 extending from proximal connector end 418 to the pressure sensor module 420 disposed near the distal end 426 of lead 412. The block diagram is very similar to the apparatus fully described in U.S. Pat. No. 5,535,752 to Halperin et al. As such, it will be generally described herein.

The monitor 300 is divided generally into an input/output circuit 312 coupled to a battery 308, an optional activity sensor 306, a telemetry antenna 334, a crystal 310, and a microcomputer circuit 314. The input/output circuit 312 includes the digital controller/timer circuit 332 and the associated components including the crystal oscillator 338, power on reset (POR) circuit 348, V ref/bias circuit 340, ADC/MUX circuit 342, RF transmitter/receiver circuit 436, optional activity circuit 352, and a pressure signal demodulator 350.

Crystal oscillator circuit 338 and crystal 310 provide the basic timing clock for the digital controller/timer circuit 332. Vref/bias circuit 340 generates stable voltage reference Vref and current levels from battery 308 for the circuits within the digital controller/timer circuit 332 and the other identified circuits, including microcomputer circuit 314 and demodulator 350. The POR circuit 348 responds to initial connection of the circuitry to the battery 308 for defining an initial operating condition and also resets the operating condition in response to detection of a low battery voltage condition. A/D converter and multiplexer circuit 342 digitizes analog signals Vprs and Vtemp received by digital controller/timer circuit 332 from demodulator 350 for storage by microcomputer circuit 314. Data signals transmitted through RF transmitter/receiver circuit 336 during telemetry are multiplexed by ADC/MUX circuit 342. Vref/bias circuit 340, ADC/MUX circuit 342, POR circuit 348, crystal oscillator circuit 338, and optional activity circuit 352 may correspond to any of those presently used in currently marketed implantable cardiac pacemakers. The digital controller/timer circuit 332 includes a set of timers and associated logic circuits connected with the microcomputer circuit 314 through the data communications bus 330.

Microcomputer circuit 314 contains an on-board chip, including microprocessor 320, associated system clock 322, and on-board RAM and ROM chips 324 and 326, respectively. In addition, microcomputer circuit 314 includes an off-board circuit 318 including separate RAM/ROM chip 328 to provide additional memory capacity. Microprocessor 320 is interrupt driven operating in a reduced power consumption mode normally and awakened in response to defined interruptive events, which may include the periodic timing out of data sampling intervals for storage of monitored data, the transfer of triggering and data signals on the bus 330, and the receipt of programming signals. A real clock and calendar function may also be included to correlate stored data to time and date.

In a further variation, provision may be made for a patient to initiate storage of monitored data through an external programmer or read switch closure when an unusual event or symptom is experienced. The monitored data may be related to an event marker on data later communicated out of the implanted device 300 to an external communication device, e.g., a programmer, which data and event marker may be examined by a physician. Microcomputer circuit 314 controls the operating functions of digital controller/timer 332 specifying which timing intervals are employed and controls the duration of various timing intervals via the bus 330. The specific current operating modes and interval values are programmable. The programmed in parameter values and operating modes are received through the antenna 334, demodulated in the RF transmifter/receiver circuit 336, and stored in RAM 324. Data transmission to and from the external device, e.g., external device 20, may be accomplished by any known manner such as those described herein.

A number of power, timing, and control signals are applied by the digital controller/timer circuit 332 to the demodulator 350 to initiate and power the operation of the pressure sensor module 420 and select a read-out of the pressure and temperature signals, Vprs and Vtemp. The voltage signals Vprs and Vtemp are converted to binary data in an ADC/MUX circuit 342. Such digital data related to pressure may be operated upon by firmware and software associated with microcomputer circuit 314 so as to implement the monitoring method according to the present invention. The monitor 300 may also optionally include a further lead connector for connection with a further lead for implantation in the right heart having an exposed unipolar distal electrode from which an electrogram (EGM) may be derived. The further lead may also have an oxygen sensor module in the distal segment of the lead.

The EGM signal may be employed to identify the onset of cardiac depolarization in each heart cycle and initiate either the monitoring and storage operations or simply initiate the storage of data derived by continuous monitoring. For example, the monitored parameters may include patient activity, e.g., heart rate, blood pressure and temperature, blood oxygen or other gas saturation levels, EGM, etc.

Blood pressure signals may preferably be digitized at a sample period of every 4 milliseconds or 256 Hz sampling frequency. The blood pressure signal may preferably be digitized and provided to the firmware for computation of physiological parameters according to the present invention. The sampled blood pressure data are absolute pressure values and do not account for changes in the barometric pressure affecting the ambient pressure load on the pressure sensor module 320. Physicians typically measure blood pressure in relation to atmospheric pressure. Thus, it may be necessary to separately record atmospheric pressure data with separate measuring and recording equipment. At present, a separate portable pressure recording unit (not shown) worn externally by the patient to record atmospheric pressure is contemplated to be used with this system and the present invention. Such information may be relayed by a communication link, as previously described herein, to the implantable medical device such that blood pressure measurements in relation to atmospheric pressure can be provided and monitored.

With use of various sensors of monitor 300, the monitor may provide signals representative of various physiological parameters such as heart rate activity, oxygen, and right ventricular pressures. Particularly, absolute pressure parameters may include systolic pressure, diastolic pressure, and estimate pulmonary artery diastolic (ePAD) pressure. The relative pressures may include pulse, maximum positive dP/dt, maximum negative dP/dt, pre-ejection interval, and systolic time interval. Although each of the physiological parameters may be monitored according to the present invention using monitor 300 adapted to implement the monitoring method described herein, the remainder of the description shall be provided relative to heart rate monitoring for which the graphical illustrations of FIGS. 7A–7D are applicable.

Figure 7A:
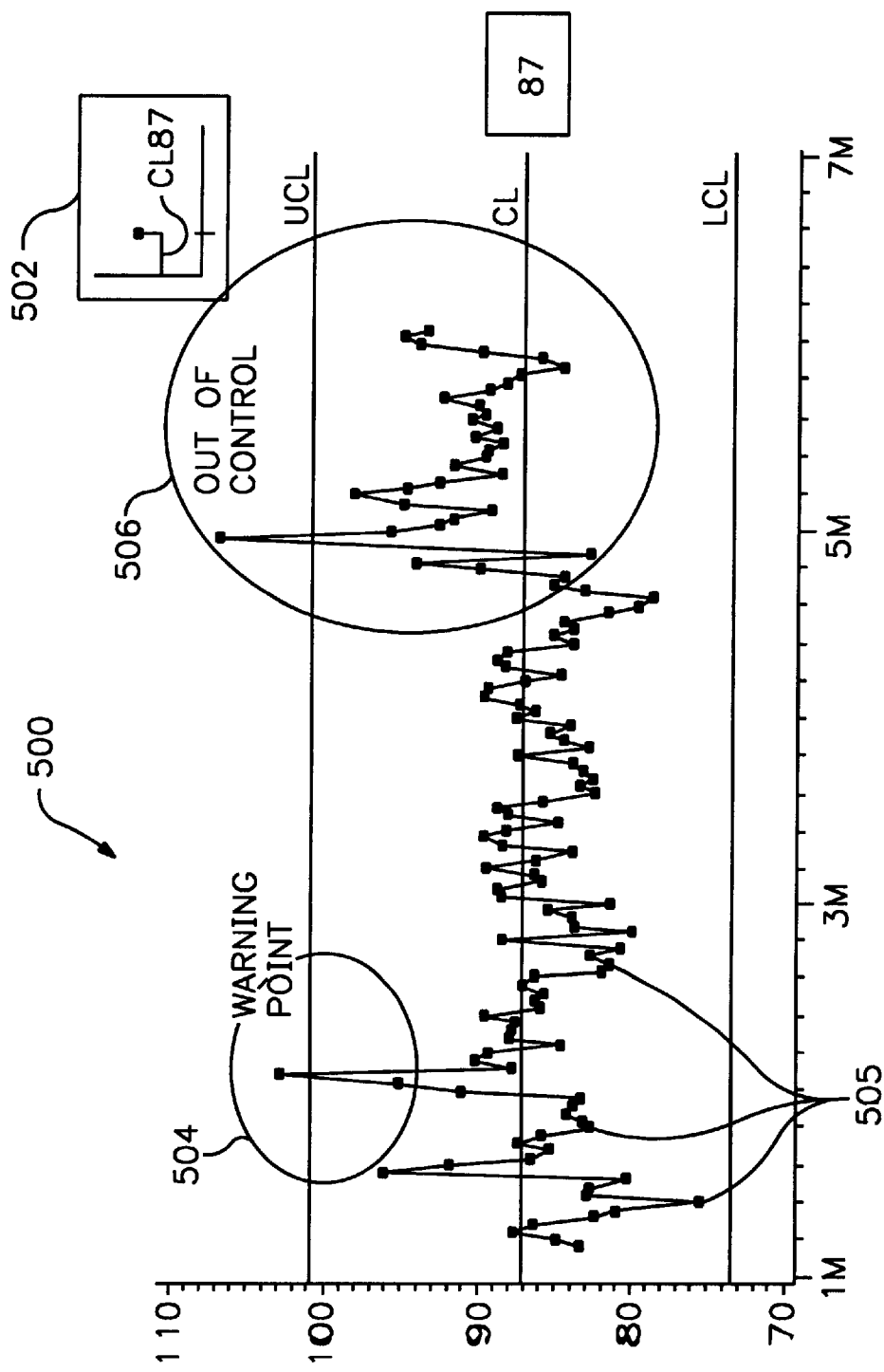
Figure 7B:
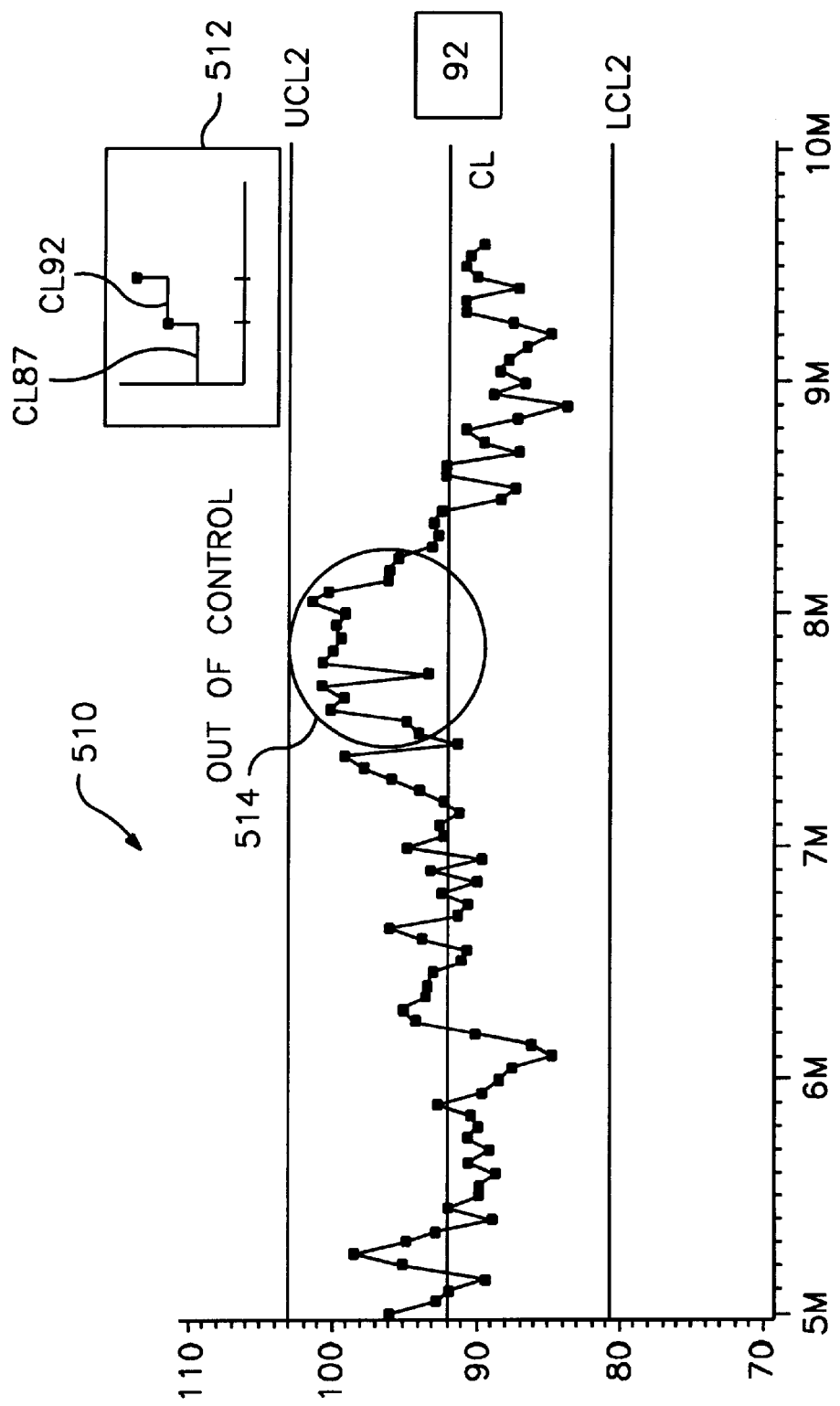

As shown in FIG. 7A, with daily average sample points 505 generated from chronic data representative of heart rate and also standard deviations provided for such chronic data relative to the daily averaged sample points 505, a centerline (CL87) is established for the heart rate parameter, i.e., a trend level of 87 beats per minute, during an initial centerline sample time period. The centerline (CL87) is established using an average of the daily average sample points 505 in the initial centerline sample time period, e.g., 15 days. An upper control limit (UCL) and lower control limit (LCL) are selected to be 3-sigma control limits, i.e., three times the average of the standard deviations calculated multiplied by a bias eliminating constant for the sampled points 505 falling in the initial centerline sample time period. Between the time 1M and the time 3M, a warning 504 is detected. A warning condition of one daily average sample point 505 above the upper control limit (UCL) is satisfied and therefore, a warning is detected. Such a warning is saved to memory for uplink to an external communication device 20 when such transfer of data from the implanted device is made. As this is only a warning, a new centerline is not re-established.

Between the time 5M and time 7M, an out of control condition 506 is satisfied detecting a change in state of the heart rate level. It is noted that the out of control conditions set to determine whether such a change in state has occurred include a first condition of fifteen consecutive points above (or below) the centerline and a second condition of eight consecutive points above (or below) the centerline with one of the sample points being above (or below) the upper control limit. As shown in FIG. 7A, both conditions are satisfied, although only one of the conditions needs to be satisfied to indicate a change in state.

Upon detection of the out of control condition indicative of a change in state of the heart rate level, data representing the centerline (CL87) is saved to memory, as represented by centerline (CL87) shown in the insert chart 502. Upon saving the centerline (CL87) to memory, a new centerline (CL92) is established using chronic data available upon or after detection of the change in state of the heart rate level, as shown in the control chart 510 of FIG. 7B. The new re-established centerline (CL92) and upper and lower control limits (UCL2/LCL2) relative to the new centerline (CL92) are calculated in substantially the same manner as the initial centerline (CL87) and upper and lower control limits (UCL/LCL). The new centerline (CL92) is determined to be at a heart rate level of 92.

At about the time 8M, another out of control condition 514 is detected indicative of a change in state of the heart rate level. In this case, fifteen consecutive points above centerline (CL92) is detected. As such, centerline (CL92) is stored in memory, as represented generally by centerline (CL92) on insert chart 512 of FIG. 7B which is shown with the prior centerline (CL87).

Figure 7C:
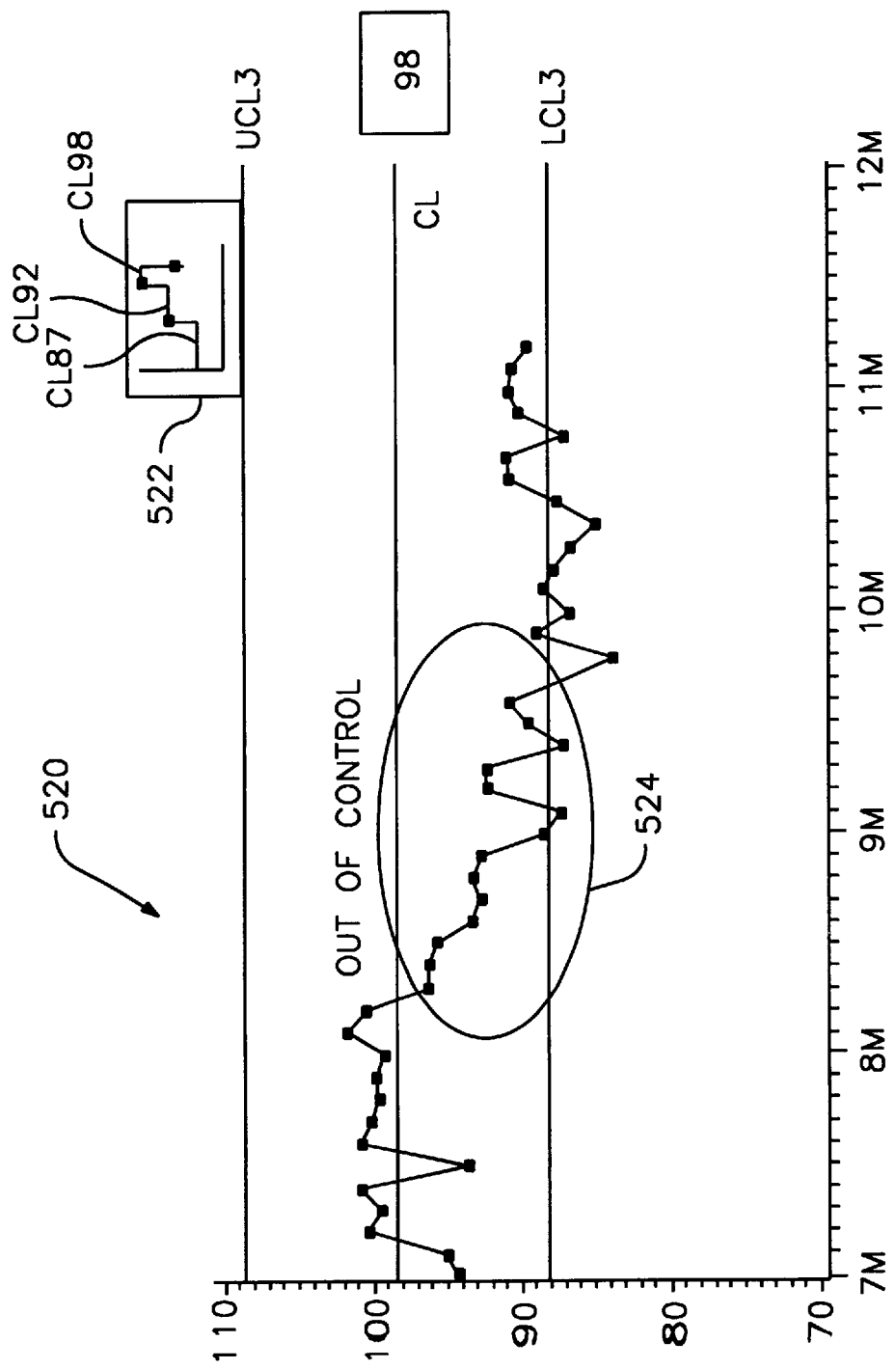

Thereafter, another centerline (CL98) and upper and lower control limits (UCL3/LCL3) are established using chronic data available upon or after detection of the change in state of the heart rate level, as shown in the control chart 520 of FIG. 7C. The chronic data associated with the heart rate is continued to be monitored. Another out of control condition 524 indicative of a change in state is detected at about the time 9M, as shown in FIG. 7C. Here, the condition of eight consecutive sample points below the centerline (CL98) with one of such sample points being below the lower control limit (LCL) is detected. Upon detection, centerline (CL98) is saved to memory as represented generally by centerline (CL98) of insert chart 522 shown in relation to the previous centerlines (CL92 and CL87). The process continues in real time with monitoring of the chronic data and saving of data associated with detected changes in state of the heart rate level. After a monitoring period is completed, such centerline data is uplinked to an external device 20.

As shown by the insert chart 522, the monitoring method 100 for monitoring the heart rate reduces the chronic data for the heart rate physiological parameter to a collection of centerlines (CL87, CL92, CL98). As such, a physician monitoring a patient having such uplinked information available can describe a proper therapy for the situation.

In FIG. 7D, a control chart 550 illustrates the reduced centerline data 552 relative to the chronic data 556 which would normally be provided to the physician in conventional devices. Such centerline data provides a much easier to follow chart which can be effectively analyzed. Further, by reducing the amount of chronic data stored in memory, a patient can be monitored for a much longer period of time without having to uplink information. It will be readily apparent to one skilled in the art from the description herein that the upper and lower control limits may also be stored and uplinked to the attending physician as an indicator of variability. This may be particularly advantageous in the case where all chronic data is discarded.

All patents and references cited herein are incorporated in their entirety as if each were incorporated separately. This invention has been described with reference to illustrative embodiments and is not meant to be construed in a limiting sense. As described previously, one skilled in the art will recognize that various other illustrative applications may utilize the monitoring method as described herein such that reduced data and desired change in status information provides significant advantages. Further, one skilled in the art will recognize that various circuit implementations may be used to carry out the monitoring method, e.g., firmware may be implemented in logic based circuits, microprocessor based functionality may be implemented in logic based circuits, firmware may be implemented using software, etc. As such, various modifications of the illustrative embodiments as well as additional embodiments of the invention will be apparent to persons skilled in the art upon reference to this description.

What is claimed is:

1. An implantable medical device monitoring method, the method comprising the steps of:

provding at least one sensor output signal to an implantable medical device;

providing chronic data representative of at least one physiological parameter based on the at least one sensor output signal;

establishing a baseline representative of an initial state of the at least one physiological parameter using chronic data provided in an initial sample time period;

monitoring the chronic data to detect a change in state of the at least one physiological parameter relative to the baseline;

storing data associated with a detected change in state of the at least one physiological parameter within the implantable medical device;

reestablishing the baseline for the at least one physiological parameter if a change in state is detected, wherein the baseline is reestablished using chronic data available upon or after detection of the change of state; and repeating the monitoring, storing, and reestablishing steps.

2. The method of claim 1, wherein monitoring the chronic data includes:

providing predetermined conditions indicative of a change in state of the at least one physiological parameter relative to the baseline; and detecting a change in state of the at least one physiological parameter relative to the baseline if the predetermined conditions are satisfied.

3. The method of claim 1, wherein establishing the baseline for the at least one physiological parameter includes:

determining a center reference line level using an average of a plurality of sample points representative of the chronic data in the initial sample time period; and determining an upper control limit and a lower control limit relative to the center reference line level based on an average of standard deviations generated for the plurality of sample points.

4. The method of claim 3, wherein monitoring the chronic data includes:

providing predetermined conditions based on the center reference line level, the upper control limit, and the lower control limit, wherein the predetermined conditions are indicative of a change in state of the at least one physiological parameter; and detecting a change in state of the at least one physiological parameter relative to the established baseline if the predetermined conditions are satisfied.

5. The method of claim 4, wherein storing data associated with the detected change in state of the at least one physiological parameter includes storing the center reference line level upon detection of a change in state of the at least one physiological parameter.

6. The method of claim 4, wherein storing data associated with the detected change in state of the at least one physiological parameter includes storing the upper and lower control limits upon detection of a change in state of the at least one physiological parameter.

7. The method of claim 4, wherein reestablishing the baseline for the at least one physiological parameter includes:

recomputing the center reference line level using an average of a plurality of sample points representative of chronic data available upon or after detection of the change of state; and recomputing the upper control limit and the lower control limit relative to the recomputed center reference line level based on an average of the standard deviations generated for the plurality of sample points representative of the chronic data available upon or after detection of the change of state.

8. The method of claim 4, wherein the predetermined conditions include at least one out of control condition indicative of a change in state of the at least one physiological parameter.

9. The method of claim 8, wherein the at least one out of control condition includes at least one out of control condition selected from the following: one or more points above an upper 3-sigma control limit; one or more points below a lower 3-sigma control limit; a run of at least eight consecutive sample points above the centerline, a run of at least eight consecutive sample points below the centerline, two of three consecutive points above an upper 2-sigma warning limit but still below the upper 3-sigma control limit; two or three consecutive sample points below a lower 2-sigma warning limit but still above the lower 3-sigma control limit; four of five consecutive points above an upper 1-sigma warning limit; four of five consecutive sample points below a lower 1-sigma warning limit; an unusual or nonrandom pattern in the sample points; and one or more points near warning limits or the 3-sigma control limits.

10. The method of claim 8, wherein the predetermined conditions further include at least one warning condition, and further wherein storing data associated with the detected change in state includes storing data associated with occurrence of a warning if the warning condition is satisfied.

11. The method of claim 1, wherein the method further includes controlling a therapeutic device in response to the detection of one or more changes in state of the at least one physiological parameter.

12. The method of claim 11, wherein the controlled therapeutic device is selected from one of a pacemaker, a brain stimulator, a defibrillator, a pacemaker/cardioverter/defibrillator, a cardioverter/defibrillator, a neurostimulator, a muscle stimulator, a gastric stimulator, a monitoring device and a drug pump.

13. The method of claim 1, wherein the method further includes controlling an alarm in response to the detection of one or more changes in state of the at least one physiological parameter.

14. The method of claim 1, wherein providing at least one sensor output signal to an implantable medical device includes providing at least one sensor output signal from an internal sensor implanted in the body to the implantable medical device and providing at least one sensor output signal from an external sensor positioned external to the body.

15. The method of claim 1, wherein the method further includes establishing a communication link with an external device located external to the body in which the implantable medical device is implanted to communicate the stored data between the implantable medical device and the external device.

16. The method of claim 1, wherein the implantable medical device is selected from one of a pacemaker, a brain stimulator, a defibrillator, a pacemaker/cardioverter/defibrillator, a cardioverter/defibrillator, a neurostimulator, a muscle stimulator, a gastric stimulator, an implantable monitor, and a drug pump.

17. The method of claim 16, wherein the medical device is an implantable hemodynamic monitor.

18. An implantable medical device monitoring method, the method comprising:

providing chronic data to an implantable medical device representative of at least one physiological parameter;

monitoring the chronic data to detect changes in state of the at least one physiological parameter;

storing data associated with detected changes in state within the implantable medical device; and discarding the chronic data monitored to detect changes in state of the at least one physiological parameter.

19. The method of claim 18, wherein monitoring the chronic data includes:

providing predetermined conditions indicative of a change in state of the at least one physiological parameter relative to a baseline established for the at least one physiological parameter; and detecting a change in state of the at least one physiological parameter if the predetermined conditions are satisfied.

20. The method of claim 19, wherein establishment of the baseline includes:

determining a center reference line level using an average of a plurality of sample points representative of chronic data over a sample time period; and determining an upper control limit and a lower control limit relative to the center reference line level based on an average of standard deviations generated for the plurality of sample points in the sample time period.

21. The method of claim 20, wherein the predetermined conditions include at least one out of control condition indicative of a change in state of the at least one physiological parameter.

22. The method of claim 21, wherein the at least one out of control condition includes at least one out of control condition selected from the following: one or more points above an upper 3-sigma control limit; one or more points below a lower 3-sigma control limit; a run of at least eight consecutive sample points above the centerline, a run of at least eight consecutive sample points below the centerline, two of three consecutive points above an upper 2-sigma warning limit but still below the upper 3-sigma control limit; two or three consecutive sample points below a lower 2-sigma warning limit but still above the lower 3-sigma control limit; four of five consecutive points above an upper 1-sigma warning limit; four of five consecutive sample points below a lower 1-sigma warning limit; an unusual or nonrandom pattern in the sample points; and one or more points near warning limits or the 3-sigma control limits.

23. The method of claim 21, wherein the predetermined conditions further include at least one warning condition, and further wherein storing data associated with the detected change in state includes storing data associated with an occurrence of a warning if the warning condition is satisfied.

24. The method of claim 21, wherein storing data associated with the detected changes in state of the at least one physiological parameter includes storing the center reference line level upon detection of a change in state of the at least one physiological parameter and thereafter reestablishing the center reference line level using an average of a plurality of sample points representative of the chronic data available upon or after detection of the change of state.

25. The method of claim 24, wherein storing data associated with the detected change in state of the at least one physiological parameter further includes storing the upper and lower control limits upon detection of a change in state of the at least one physiological parameter.

26. An implantable monitoring system for monitoring at least one physiological parameter, the system comprising:

at least one sensor to provide an output signal representative of the at least one physiological parameter; and an implantable monitoring device having memory to store data, wherein the implantable monitoring device further includes:

means for receiving the at least one sensor output signal and generating chronic data representative of the at least one physiological parameter; and processing means for monitoring the chronic data to detect changes in state of the at least one physiological parameter and for storing data associated with detected changes in state in the memory of the implantable monitoring device, the processing means including:

means for establishing a baseline representative of an initial state of the at least one physiological parameter using a plurality of sample points representative of chronic data in an initial sample time interval;

means for detecting changes in state of the at least one physiological parameter relative to the baseline; and means for reestablishing the baseline for the at least one physiological parameter if a change in state is detected, wherein the baseline is reestablished using chronic data available upon or after detection of the change of state.

27. The system of claim 26, wherein the means for detecting changes in state of the at least one physiological parameter relative to the baseline includes:

means for comparing sample points representative of the chronic data to the baseline; and means for determining if the comparison satisfies predetermined conditions indicative of a change in state of the at least one physiological parameter.

28. The system of claim 27, wherein the means for establishing the baseline for the at least one physiological parameter includes:

means for averaging the plurality of sample points representative of chronic data in an initial sample time interval to determine a center reference line level; and means for averaging the standard deviations of the plurality of sample points representative of chronic data in an initial sample time interval for use in determining an upper control limit and a lower control limit relative to the center reference line level.

29. The system of claim 28, wherein the predetermined conditions are based on the center reference line level, the upper control limit, and the lower control limit.

30. The system of claim 28, wherein data stored in memory associated with the detected change in state of the at least one physiological parameter includes data representative of the center reference line level.

31. The system of claim 30, wherein data stored in memory associated with the detected change in state of the at least one physiological parameter further includes data representative the upper and lower control limits.

32. The system of claim 28, wherein means for reestablishing the baseline for the at least one physiological parameter includes:

means for recomputing the center reference line level using an average of a plurality of sample points representative of chronic data available upon or after detection of the change of state; and means for recomputing the upper control limit and the lower control limit relative to the recomputed center reference line level based on an average of standard deviations generated for the plurality of sample points representative of chronic data available upon or after detection of the change of state.

33. The system of claim 27, wherein the predetermined conditions include at least one out of control condition indicative of a change in state of the at least one physiological parameter.

34. The system of claim 33, wherein the at least one out of control condition includes at least one out of control condition selected from the following: one or more points above an upper 3-sigma control limit; one or more points below a lower 3-sigma control limit; a run of at least eight consecutive sample points above the centerline, a run of at least eight consecutive sample points below the centerline, two of three consecutive points above an upper 2-sigma warning limit but still below the upper 3-sigma control limit; two or three consecutive sample points below a lower 2-sigma warning limit but still above the lower 3-sigma control limit; four of five consecutive points above an upper 1-sigma warning limit; four of five consecutive sample points below a lower 1-sigma warning limit; an unusual or nonrandom pattern in the sample points; and one or more points near warning limits or the 3-sigma control limits.

35. The system of claim 33, wherein the predetermined conditions further include at least one warning condition, and further wherein the processing means includes means for storing data in the memory associated with an occurrence of a warning if the warning condition is satisfied.

36. The system of claim 26, wherein the system further includes a therapeutic device, and further wherein the processing means further includes means for controlling the therapeutic device in response to the detection of one or more changes in state of the at least one physiological parameter.

37. The system of claim 36, wherein the controlled therapeutic device is selected from one of a pacemaker, a brain stimulator, a defibrillator, a pacemaker/cardioverter/defibrillator, a cardioverter/defibrillator, a neurostimulator, a muscle stimulator, a gastric stimulator, a monitoring device and a drug pump.

38. The system of claim 26, wherein the system further includes an alarm device, and further wherein the processing means further includes means for controlling the alarm device in response to the detection of one or more changes in state of the at least one physiological parameter.

39. The system of claim 26, wherein the at least one sensor includes an internal sensor for implant in the body for generating a sensor output signal to the implantable monitoring device and an external sensor for positioning external to the body to generate at least one sensor output signal for communication to the implantable monitoring device.

40. The system of claim 26, wherein the implantable monitoring device is a portion of an implantable medical device selected from one of a pacemaker, a brain stimulator, a defibrillator, a muscle stimulator, a pacemaker/cardioverter/defibrillator, a cardioverter/defibrillator, a neurostimulator, a gastric stimulator, an implantable monitor, and a drug pump.

41. The system of claim 40, wherein the implantable monitoring device is an implantable hemodynamic monitor.

* * * * *